United States Patent [19]

Takata et al.

[11] Patent Number: 4,576,706
[45] Date of Patent: Mar. 18, 1986

[54] FLOWTHROUGH-TYPE ELECTROLYTIC CELL

[75] Inventors: Yoshinori Takata, Chiba; Mamoru Taki, Ibaraki, both of Japan

[73] Assignee: Hitachi, Ltd., Tokyo, Japan

[21] Appl. No.: 647,483

[22] Filed: Sep. 5, 1984

[30] Foreign Application Priority Data

Sep. 5, 1983 [JP] Japan ................................. 58-162786

[51] Int. Cl.$^4$ ............................................. G01N 27/42
[52] U.S. Cl. ................................. 204/409; 73/61.1 C; 422/70
[58] Field of Search ............. 204/405, 409, 1 T, 1 M; 73/61.1 C; 422/70; 436/151

[56] References Cited

U.S. PATENT DOCUMENTS 3,846,270 11/1974 Muro et al. .......................... 204/405
4,149,950 4/1979 Potts ................................... 204/409

FOREIGN PATENT DOCUMENTS 1394358 5/1975 United Kingdom ................ 204/409

OTHER PUBLICATIONS

Gary W. Schieffer, Anal. Chem., vol. 51, No. 9, pp. 1573-1575, Aug. 1979.

W. Lowry Caudill et al., Anal. Chem. vol. 54, No. 14, pp. 2532-2535, Dec. 1982.

*Primary Examiner*—G. L. Kaplan
*Attorney, Agent, or Firm*—Antonelli, Terry & Wands

[57] ABSTRACT

A sample leaving a separation column of liquid chromatograph is led to an electrolytic cell to obtain an electrolytic current corresponding to the amount of an assayed sample component. The electrolytic cell is divided into two compartments by an ion exchange pipe penetrating therethrough at the center. One compartment is a cylindrical working electrode chamber in the pipe, and the other compartment is a cylindrical chamber for a counterelectrode outside the pipe. A working electrode comprising a bundle of electroconductive carbon fibers is provided in the working electrode chamber, and preferably a swellable rod is inserted as a core into the working electrode. In the chamber for the counterelectrode, a cylindrical counterelectrode made of carbon fibers is provided to surround the outside surface of the ion exchange pipe. The inner diameter of the ion exchange pipe is substantially equal to the inner diameter of a tube for introducing the sample. The sample undergoes electrolysis reaction while the sample passes through the carbon fibers of the working electrode.

27 Claims, 14 Drawing Figures

FLOWTHROUGH-TYPE ELECTROLYTIC CELL

BACKGROUND OF THE INVENTION

This invention relates to a flowthrough-type electrolytic cell, and particularly to an electrolytic cell suitable for detecting sample components in a sample solution by constant potential electrolysis.

Conventional, flowthrough-type electrolytic cells are disclosed, for example, in U.S. Pat. No. 3,846,270, where a controlled potential coulometry cell has a working electrode of plate-like shape and two counterelectrodes of similar shape, and the working electrode is sandwiched between two ion exchange membranes. In such a conventional electrolytic cell, the thickness of the electrode cannot be made extremely smaller due to the use of porous electrodes of plate-like shape, and thus the cell capacity is as large as about 200 µl. Furthermore, such a conventional electrolytic cell has unworking electrode parts, which fail to work effectively for the electrolysis, for example, the side parts and the parts counterposed to the counterelectrodes.

SUMMARY OF THE INVENTION

An object of the present invention is to provide a flowthrough-type electrolytic cell with an increased detection sensitivity to sample components.

Another object of the present invention is to provide a flowthrough-type electrolytic cell of a smaller cell volume and a higher performance.

Another object of the present invention is to provide a flowthrough-type electrolytic cell which can prevent a void formation in a working electrode chamber against swelling of ion exchange pipe means that isolates the working electrode from the counterelectrode.

Still another object of the present invention is to provide a flowthrough-type electrolytic cell which can automatically regenerate the counterelectrodes or electrolytic solution by dissolved oxygen from the air.

It is one feature of the present invention that a sample can flow through an ion exchange pipe means, for which a cation exchange tube or an anion exchange tube can be selected in view of the species of sample components.

It is another feature of the present invention that a working electrode is provided in the ion exchange pipe means, and a counterelectrode is provided outside the ion exchange pipe means, where the working electrode is preferably an assembly or a bundle of fine linear or small granular electroconductive materials. Cross-sectional shape of the ion exchange pipe can be not only circular, but also triangular, polygonal, elliptical, etc. in view of easier packing of the working electrode and the species of packing materials.

According to a preferable embodiment of the present invention, the cross-sectional area of the hollow part of the ion exchange pipe is substantially equal to the cross-sectional area of a conduit for leading a sample to the electrolytic cell. That is, the cross-sectional area of the hollow part of the ion exchange pipe is not so large as three times the cross-sectional area of the conduit. With this structure, diffusion of a sample can be prevented within the electrolytic cell, and remixing of separated sample components can be reduced.

According to a further embodiment of the present invention, the working electrode is firmly packed in the ion exchange pipe, so that no voids may be formed between the outside surface of the working electrode and the inside surface of the ion exchange pipe.

For much higher preciseness in measurement, a rod-like material can be inserted into the working electrode to prevent formation of voids between the working electrode and the ion exchange pipe. The rod-like material for the insertion may be an electroconductive rod or may be a material having a swelling characteristics equal to that of the ion exchange pipe.

According to still further embodiment of the present invention, at least one part of the outside wall of the chamber that contains an electrolytic solution is made of an oxygen-permeable material to take in the oxygen from the atmospheric air. Reduction product from the electrochemical reaction in the electrolytic cell is oxidized by the dissolved oxygen that has been permeated through the oxygen-permeable membrane, whereby the counterelectrode or the electrolytic solution can be automatically regenerated.

Other objects and features of the present invention will be apparent from the disclosure which follows.

DETAILED DESCRIPTION OF THE PREFERRED EMBODIMENTS

Figure 1:
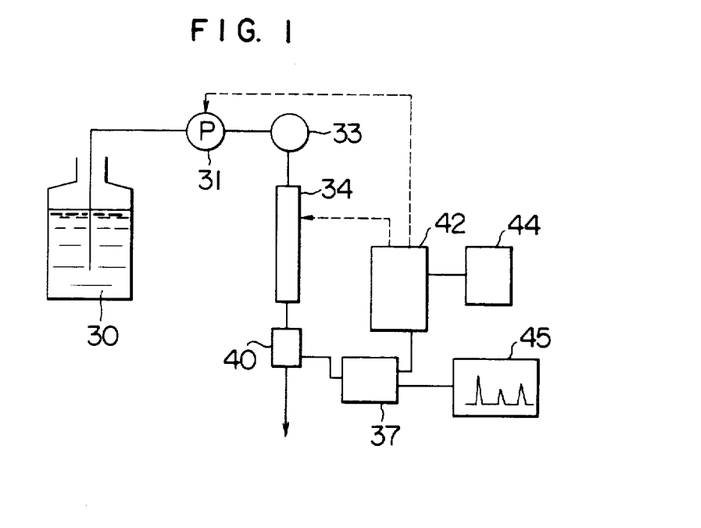
FIG. 1 is a schematic flow diagram showing an example of a liquid chromatograph to which the present invention is applied.

In FIG. 1, an electrolytic cell 40, to which the present invention is applied, is provided at the downstream of a separation column 34. An eluant solution 30 is introduced into the separation column 34 through a sample feed point 33 through a solution feed pump 31. Flow rate of the pump 31 and temperature elevation of the separation column 34 are controlled by a microcomputer 42. A constant potential-applying device 37 including a current amplifier gives a constant potential to the electrodes of the electrolytic cell 40 according to the species of samples or sample components and outputs the electrolytic current flowed according to the concentrations of sample components to the microcomputer 42 upon amplification. Current change analog signals are recorded by a recorder 45, and the concentrations of the respective sample components calculated by the computer 42 are displayed on a display device, for example, a printer 44. Various kinds of eluant solution 30 can be used.

Figure 3:
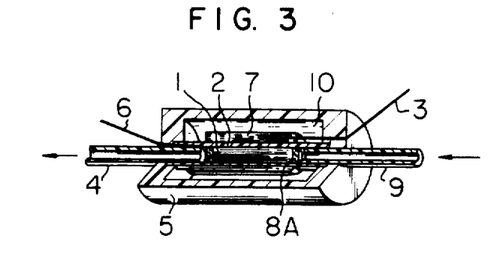
FIG. 3 is a partially cut-away perspective view of the embodiment of FIG. 2.
Figure 4:
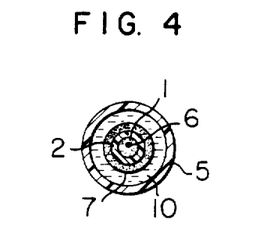
FIG. 4 is a cross-sectional view along the line IV—IV of FIG. 2.

A first embodiment of the present invention will be described, referring to FIGS. 2 to 4.

One end of a cation exchange pipe 2 is connected to a fluorine resin tube 9 which serves as a sample inlet conduit, and the other end of the pipe 2 is connected to a fluorine resin tube 4 which serves as a sample outlet conduit. A columnar working electrode 1 is provided in the cation exchange pipe 2, and a cylindrical counterelectrode 7 is provided around the pipe 2. As the ion exchange pipe 2, a tube commercially available, for example, from DuPont Co. (USA) as Nafion tube 811X can be used.

The working electrode is so formed that there may be no voids between the outside surface of the working electrode 1 and the inside surface of the ion exchange tube 2. The working electrode is made of an assembly or bundle of fine fibers or small particles of an electroconductive material. According to the first embodiment, a bundle of electroconductive carbon fibers as working electrode material is packed so that the longitudinal direction of the fibers can conform to the longitudinal direction of the ion exchange tube 2. Filters 8A and 8B are provided at the ends of the working electrode.

The counterelectrode is provided at the outside of the ion exchange tube 2 so as to surround the outside surface of the tube 2. The counterelectrode material is a bundle of electroconductive carbon fibers (glassy carbons), placed upon one another to a desired thickness, and wound by a platinum wire, and is fixed to the ion exchange tube 2. Case 5 of the electrolytic cell 40 is made of an electric insulator, for example, transparent plastic. In the case 5, the ion exchange tube 2 is provided so as to penetrate the case 5. Thus, a cylindrical chamber 10 is formed between the inside surface of case 5 and the outside surface of tube 2, and is filled with an electrolytic solution. A lead wire 6 is connected to the working electrode 1 and another lead wire 3 is connected to the counterelectrode 7.

When the electrolytic cell 40 is used as a detector for a liquid chromatograph as in FIG. 1, a liquid containing electroactive substances as an effluent from the separation column 34 flows through the tube 9 and passes through the filter 8A, the working electrode 1, the filter 8B and the tube 4 to the outside. The working electrode 1 is a bundle of carbon fibers (glassy carbons) each having a diameter of 7 μm, and almost ten thousand of the fibers are packed in the cation exchange tube 2 having an inner diameter of 0.8 mm. The length of the working electrode is about 8 mm and the inner capacity of it is about 2 μl.

In the electrolytic solution chamber 10, an alkaline solution mixture containing 0.2 moles/l of potassium ferricyanide, 0.2 moles/l of potassium ferrocyanide and 0.2 moles/l of $KNO_3$ is provided as an electrolytic solution for the counterelectrode 7. A predetermined potential is applied to both electrodes through the lead wires 3 and 6 from the outside. When a potential high enough for the constant potential electrolysis of a desired electroactive substance is applied thereto, the electroactive substance in the solution as introduced through the tube 9 is substantially 100% electrolyzed until it flows out of tube 4. In this embodiment, substantially 100% efficiency can be attained at a flow rate of up to 1.5 ml/min.

Figure 5:
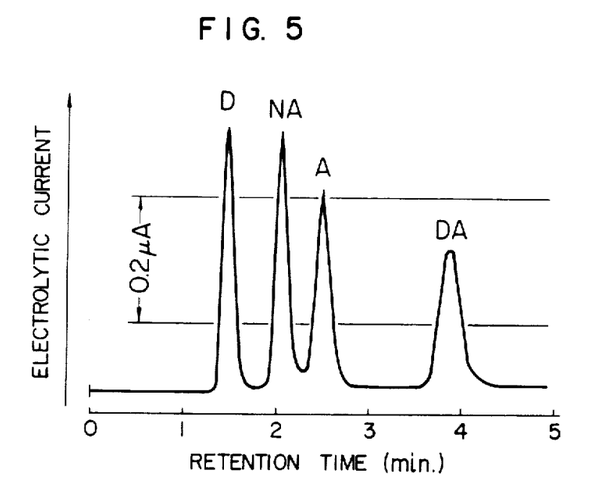
FIG. 5 is a chromatogram obtained when the embodiment of FIG. 2 is applied to FIG. 1 as a detector.

A chromatogram obtained by chromatographically separating a catecholamine sample with such an electrolytic cell and measuring the separated components is shown in FIG. 5, where the axis of abscissa shows retention time and the axis of ordinate shows an electrolytic current flowed between the electrodes 1 and 7. Measurement conditions for the chromatography is shown in Table 1. In FIG. 5, dopa (D), noradrenaline (NA), adrenaline (A) and dopamine (DA) are detected.

TABLE 1

Measurement conditions for chromatography
Sample: catecholamine, $2.5 \times 10^{-11}$ moles
Separation column: Hitachi gel 3013C, 4 mm ID × 5 mm high
Column temperature: room temperature
Eluant solution: aqueous 0.1M $CH_3COOH$-2% $CH_3CN$ solution
Flow rate of eluant solution: 1.0 ml/min.
Detection potential: 0.6 V vs Ferri-Ferro cyanide In this chromatography, 25 picomoles of catecholamine can be detected with a detection sensitivity (S/N=2) of about tens of picograms.

Figure 2:
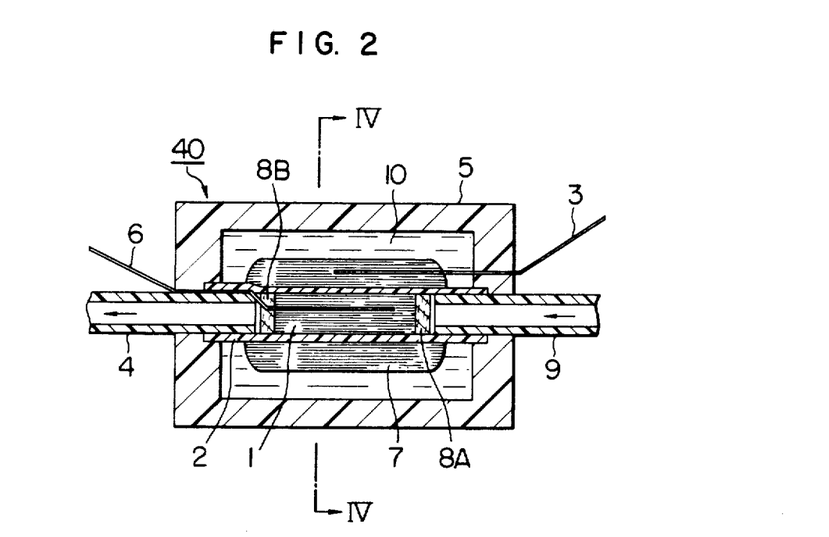
FIG. 2 is a cross-sectional view according to a first embodiment of the present invention.

In the embodiment shown in FIG. 2, glassy carbon fibers are used for the working electrode 1 and the counterelectrode 7. Any other material can be also used in place of the glassy carbon fibers in view of a desired purpose, so long as it is an electroconductive material. For example, when silver is used for the working electrode 1, cyanide ions or halide ions can be detected, and when copper is used for the working electrode 1, amino acids, etc. can be detected. Furthermore, gold or platinum can be used for the general purpose. That is, working electrode material can be selected in view of desired detection purposes. On the other hand, the counterelectrode 7 must be in a non-polarizable structure or must be made of non-polarizable material. For example, when an electrochemically, relatively stable material such as carbon, gold, platinum, etc. is used for the counterelectrode, possible polarization can be prevented by using a solution mixture of ferricyanide-ferrocyanide as the electrolytic solution. When a silver-silver chloride electrode having a large surface area is used for the counterelectrode, an aqueous chloride solution can be used as the electrolytic solution. Furthermore, a silver-silver iodide electrode, a silver-silver bromide electrode, etc. can be used for the counterelectrode 7.

In this embodiment, the fibers having a diameter of 7 μm are used for the working electrode 1, but the working electrode material may be in a wire or granular form. If they are coarse, for example, more than 100 μm in diameter, the working electrode 1 must be made considerably longer, and this is not practical.

When the ion exchange tube 2 has a diameter of more than 1 mm, the central part of the working electrode 1 will not work effectively, so that a portion of the electroactive substance may pass through the tube 2 without any electrolysis and it will be difficult to maintain substantially 100% electrolytic efficiency. However, so long as the conditions are constant, substantially constant electrolytic efficiency can be obtained, and thus such an electrolytic cell can also serve, for example, as a detector for a liquid chromatography.

So long as the electrolytic efficiency is substantially 100%, the weight W of a desired electroactive substance can be calculated from the Faraday's law ($\theta = nF$ W/M) by measuring a quantity of electricity $\theta$ which has flowed during the electrolysis of the electroactive substance, where n is the number of electrons taking part in the oxidation and reduction; F is a Faraday constant, i.e. about 96,500 coulombs/equivalent; M is a molecular weight. Particularly in the chromatogram, it is an advantage that a peak area directly shows a quantity of electricity, and thus the amount of a desired component can be directly obtained without using any working curve.

It is often necessary to exchange the electrolytic solution for the counterelectrode. To avoid such a troublesome exchange, the case 5 is provided with an inlet and an outlet for the electrolytic solution so that the electrolytic solution for the counterelectrode can be made to flow therethrough by a pump, etc.

Thus, in this embodiment, the working electrode can be made to work effectively, so that the electrode area can be made smaller than that of the conventional one, and thus the volume of an electrolytic cell can be considerably reduced. This is an effect of this embodiment when the present flowthrough-type electrolytic cell is applied, for example, as a detector for a liquid chromatography, an expansion of a peak in the detector, that is, at the outside of the separation column, can be prevented. Furthermore, the smaller electrode area can lower the background electric current and thus reduce a noise, and can perform detection with a high sensitivity. These are the secondary effects of this embodiment.

With the working electrode provided in the ion exchange pipe, the electrolytic reaction mainly occurs at the inside of the working electrode only down to an inner depth of about 15 $\mu$m from the outside surface of the working electrode. Thus, to improve the electrolytic efficiency, a sample solution must be prevented from passing through and along the central part or its neighbor of the working electrode. In the present invention, a packing is provided at the central part or its neighbor of the working electrode to improve the electrolytic efficiency, making the inner cell volume smaller. As a packing, a rod-like material, is used which can preferably reach one end to another of the working electrode.

One example of the material for such a rod-like material is an electroconductive material, such as a platinum wire, and another example thereof is a material that can swell with an aqueous solution, such as an ion exchange resin rod. In a case of using the electroconductive rod-like material, the lead wire for the working electrode is connected to the rod-like material.

Figure 6:
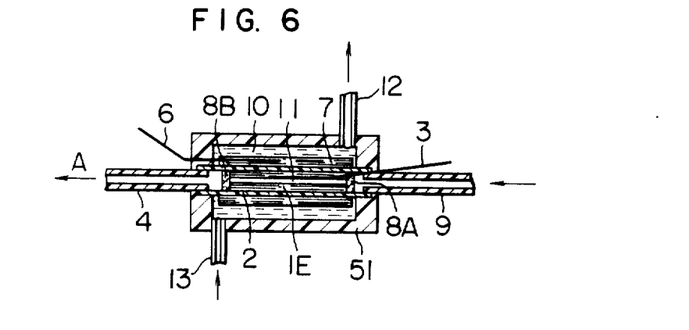
FIG. 6 is a cross-sectional view according to a second embodiment of the present invention.
Figure 7:
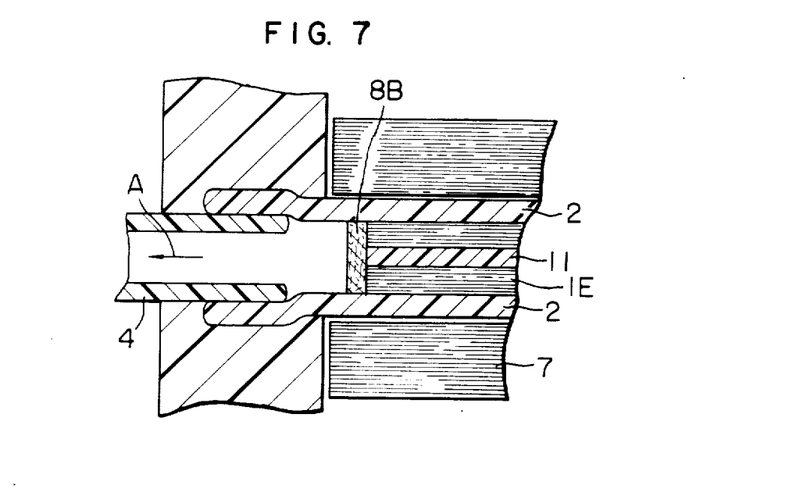
FIG. 7 is a cross-sectional view of the essential part in the embodiment of FIG. 6.

In FIGS. 6 to 7, a second embodiment of the present invention is shown, where a material, which can swell as equally as or more than the ion exchange pipe, is inserted at the central part of the electroconductive material packed in the ion exchange pipe 2.

In an electrolytic cell with an electroconductive material packed in the ion exchange pipe to work as a working electrode, as shown in FIG. 2, the ion exchange pipe swells through contact with an aqueous solution and voids are formed between the packed electrode and the inside surface of the pipe in the said ion exchange pipe. The solution can by-pass through the voids, and no 100% electrolytic efficiency can be often attained. According to the embodiment of FIG. 6, such an inconvenience can be eliminated.

That is, a material, which can swell as equally as or more than the ion exchange pipe, is inserted at the central part of the electroconductive material packed in the ion exchange pipe, and when the ion exchange pipe 2 is swollen to expand its inner diameter, the inserted material can press and extend the electroconductive material toward the pipe wall to prevent formation of the voids in the pipe.

In the embodiment of FIG. 6, a working electrode 1E surrounds an ion exchange resin rod to make a cylindrical shape, where a bunde of several thousand of glassy carbon fibers, each having a diameter of about 7 $\mu$m, is packed to a length of 8 mm in a cation exchange pipe 2 having an inner diameter of 0.8 mm as swollen, and an ion exchange resin rod is inserted as a swelling material 11 at the cental part of the bundle. They are prevented from flowing-away by filters 8A and 8B. A sample solution for electrolysis is led to an inlet through a fluorine resin solution conduit (tube) 9, passes through the filter 8A to the working electrode 1E and flows in the arrow direction A. The ion exchange pipe 2 swells through contact with the solution and expands outwards. At the same time, the swelling material 11 swells and pushes the working electrode 1 toward the side wall of the ion exchange pipe 2. Thus, formation of voids in the electrode 1 and the resulting jolting of electrode or the resulting by-passing of the solution through voids and insufficient contact with the electrode can be prevented thereby.

In the embodiment of FIG. 6, an electrolytic solution flows through an electrolytic solution chamber 10. That is, the electrolytic solution is introduced through an inlet 13 and discharged through an outlet 12. A counterelectrode 7 can be a non-polarizable electrode which can also work as a reference electrode, and constant potential electrolysis of two-electrode type can be carried out by applying a constant voltage to between the non-polarizable electrode and the working electrode 1E.

On the other hand, a suitable reference electrode, such as Ag-AgCl, etc. can be provided in the solution conduit (tube) 4 and/or 9 through a liquid junction, and constant potential electrolysis of three-electrode type can be carried out with a potentiostat.

Thus, in the embodiment of FIG. 6, such a flow-through-type electrolytic cell can be effectively provided, which has none of such troubles as formation of voids between the inside wall of ion exchange pipe 2 as a membrane and the working electrode due to the swelling of pipe 2, lowered electrolytic efficiency, jolting of the working electrode with a result of a noise source, and poor contact with the lead wire.

Figure 13:
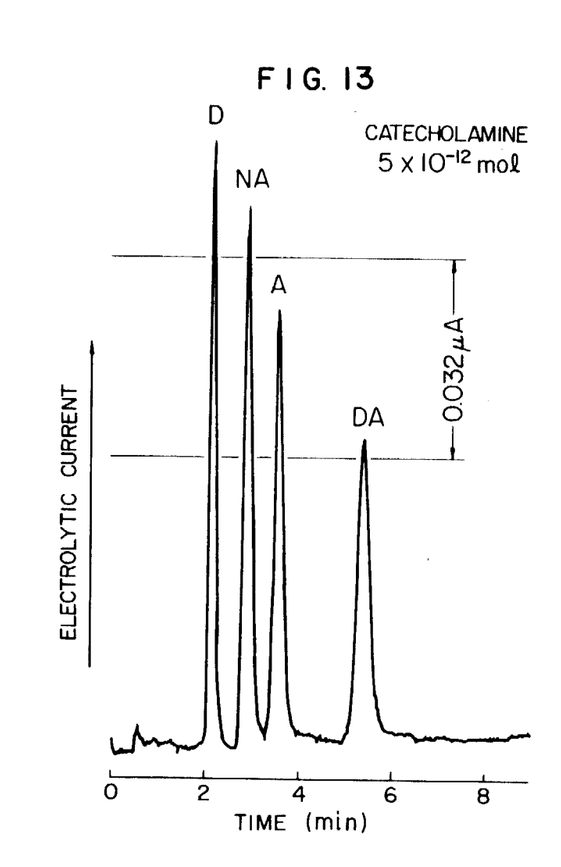
FIG. 13 is a diagram showing measurement results of a low concentration sample according to the embodiment of FIG. 6.

FIG. 13 shows a chromatogram obtained by measuring catecholamine with an apparatus embodied in FIG. 6, where the amount of catecholamine is $5 \times 10^{-12}$ moles and the flow rate is 1 ml/min.

Figure 14:
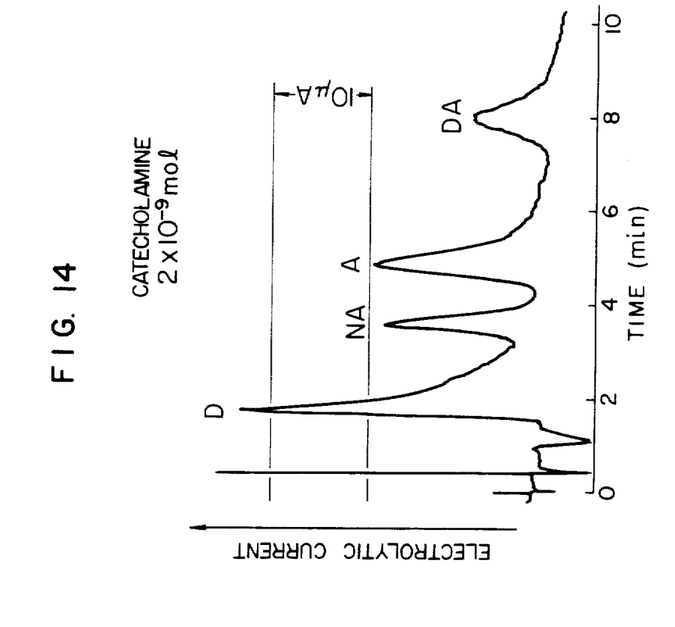
FIG. 14 is a diagram showing measurement results of high concentration sample when a conventional coulometric monitor is used for comparison with FIG. 13.

FIG. 14 is a chromatogram obtained for comparison by measuring catecholamine with the conventional coulometric monitor, where the conventional coulometric monitor uses an electrolytic cell of such a structure that a plate-like working electrode is sandwiched between two plate-like counterelectrodes through plate-like ion exchange membranes.

In FIG. 14 with the conventional apparatus, the amount of catecholamine is $2 \times 10^{-9}$ moles, which is 400 times as high as the concentration in FIG. 13, but the base line fluctuation is larger. The flow rate in FIG. 14 is 0.6 ml/min.

In the example of FIG. 13 according to the present invention, detection is possible even if the electric current has a very small peak of $3 \times 10^{-3}$ μA, whereas in the example of FIG. 14 a detection of 1 μA is only possible.

Figure 8:
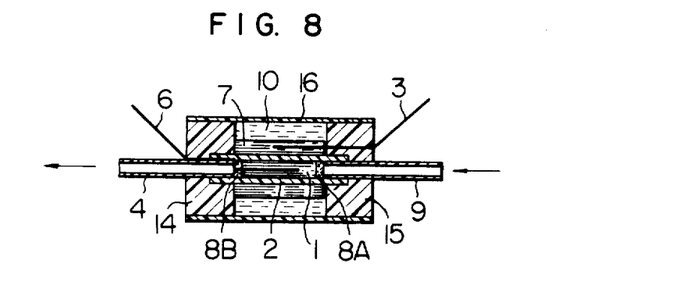
FIG. 8 is a cross-sectional view according to a third embodiment of the present invention.

In FIG. 8, a third embodiment of the present invention is shown, where a working electrode 1 is provided in a cation exchange pipe 2 and filters 8A and 8B are provided at both ends of the working electrode 1. Tubes 4 and 9 are connected to the ion exchange pipe 2. A counterelectrode 7 and an electrolytic solution chamber 10 are provided around the cation exchange pipe 2. Ring-like cell frames 14 and 15 are fixed to connection parts between the cation exchange pipe 2 and the tube 4 and 9, respectively. An oxygen-permeable membrane 16 is provided around the cell frames to cover both cell frames. A lead wire 6 is connected to the working electrode 1, and a lead wire 3 is connected to the counterelectrode 7.

A predetermined potential is applied to between the working electrode and the counterelectrode to selectively electrolyze a desired component. A solution containing electroactive substances is led through the tube 9, the filter 8A, the working electrode 1, the filter 8B and the tube 4 to the outside. On the other hand, at the counter electrode side, an Ag-AgI electrode and a KI solution are used as the counterelectrode 7 and the electrolytic solution for the counterelectrode, respectively, and are reduced at the detection of a desired component and Ag is spontaneously oxidized again with the dissolved oxygen. Its detail will be described later. Dissolvable oxygen is always supplied to the counterelectrode chamber from the atmospheric air through the oxygen-permeable membrane 16. In this embodiment, the oxygen-permeable membrane is a silicone rubber membrane having a thickness of 0.5 mm, but polytetrafluoroethylene, etc. can be also used. The working electrode 1 is a bundle of almost ten thousand of electroconductive glassy carbon fibers, each having a diameter of 7 μm, which is packed in a cation exchange pipe having an inner diameter of 0.8 mm.

When it is desired to detect very small amounts of components contained in a living body, such as catecholamine, the quantity of passing electricity is as small as about 5 microcoulombs, even if there are relative large amounts of the components such as about 25 picomoles. Furthermore, the background current amounts to not more than 0.5 μA in the electrolytic cell of this embodiment, and thus the quantity of passing current amounts to not more than 18 millicoulombs, even if the electric current is passed continuously for 10 hours. This corresponds to formation of about 20 μg of Ag in terms of the following electrochemical reaction equation (1):

$$AgI + e \rightarrow Ag + I^- \quad (1)$$

Thus, there will be no trouble in automatic regeneration of Ag by the dissolved oxygen for the remaining 14 hours which corresponds to the rest time of the flow-through-type electrolytic cell, if 1 μl of oxygen can be dissolved into the electrolytic solution in the chamber for the counterelectrode for 14 hours, that is, at a rate of about $4 \times 10^{-9}$ cc/sec. of oxygen, as is evident from the following reaction equation (2):

$$2Ag + 2I^- + \tfrac{1}{2}O_2 + H_2O \rightarrow 2AgI + 2OH \quad (2)$$

On the other hand, the permeation rate q of a polymeric material for 1 cm³ of oxygen gas can be calculated according to the following equation (3):

$$g \ (cc/cm.sec) = k(P_1 - P_2)/l \quad (3)$$

wherein $P_1$ and $P_2$ are pressures (cmHg) on both sides of the membrane; l is a thickness (cm) of the membrane; k is a constant of at least $10^{-8}$ cc.cm/cm².sec.cmHg in the case of a membrane having a good permeability such as silicone rubber, etc. Thus, in the case of a silicone rubber plate having a thickness of 1 mm, the oxygen can be dissolved at a rate of $10^{-7}$ cc/sec/cm², even if a pressure difference is about 1 cmHg. This is quite satisfactory.

In the embodiment of FIG. 8, a fresh electrolytic solution is always introduced into the electrolytic solution chamber for the counterelectrode, and thus the solution feed pump is required. On the other hand, in the embodiment of FIG. 8, a combination of members which can be reduced at the detection of a desired sample component and spontaneously oxidized by the dissolved oxygen, such as an Ag-AgI electrode and a KI solution, is selected as a combination of the counterelectrode and the electrolytic solution for the counterelectrode, and silicone rubber having a thickness of about 1 mm is used as a material for forming the electrolytic solution chamber for the counterelectrode, whereby exchange of the counterelectrode or the electrolytic solution for the counterelectrode can be made unnecessary.

Figure 9:
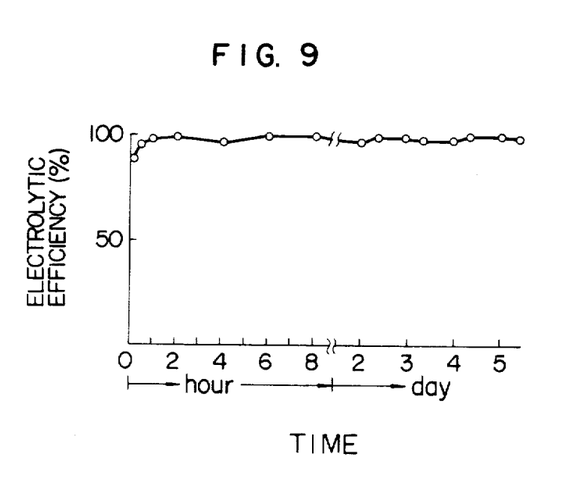
FIG. 9 is a diagram showing changes in electrolytic efficiency with time when the embodiment of FIG. 8 is applied.

FIG. 9 shows data for proving regeneration of an electrolytic solution when an apparatus embodied in FIG. 8 is used. That is, the results of measuring electrolytic efficiency with a catecholamine sample for 5 days are shown in FIG. 9. Chromatographic measurement conditions for this purpose are shown in Table 2:

TABLE 2

Sample: Dopamine, $2.5 \times 10$
Separation column: Hitachi gel #3013-C, 4 mm ID × 50 mm high
Column temperature: room temperature
Eluant solution: 0.1 MCH₃COOH-2% CH₃CN
Eluant solution flow rate: 1.0 ml/min.
Detection potential: 1.0 V vs. Ag-AgI
Electrolytic solution for counterelectrode: 1M KI In Table 2, Hitachi gel #3013-C is a cation exchange resin of styrene-divinylbenzene copolymer with particle sizes of 5 to 7 μm.

In FIG. 9, the axis of abscissa shows a change in time and the axis of ordinate shows an electrolytic efficiency, where results of less fluctuation are shown for 8 hours and also for 5 days. It is evident from these results that the automatic regeneration is carried out at the counterelectrode of the flow-type electrolytic cell embodied in FIG. 8.

By using an oxygen-permeable material such as silicone rubber, etc. having a thickness of 0.5 to 1 mm as a material for forming an outside wall of an electrolytic cell and also by selecting a combination of members which can be reduced at the detection of a desired sample component and spontaneously oxidized by the dissolved oxygen, such as an Ag-AgI electrode and a KI solution as a combination of the counterelectrode and the electrolytic solution for the counterelectrode, as in the embodiment of FIG. 8, an effect of making unnecessary the exchange of counterelectrode or electrolytic solution for the counterelectrode can be obtained. Furthermore, such secondary effects can be obtained as a reduction in the flow noise at the counterelectrode and an increase in the detection sensitivity owing to no continued introduction of a fresh electrolytic solution for the counterelectrode, and also a reduction in the apparatus size owing to no requirement for any feed pump for the electrolytic solution for the counterelectrode, and the resulting reduction in a detector cost.

Figure 10:
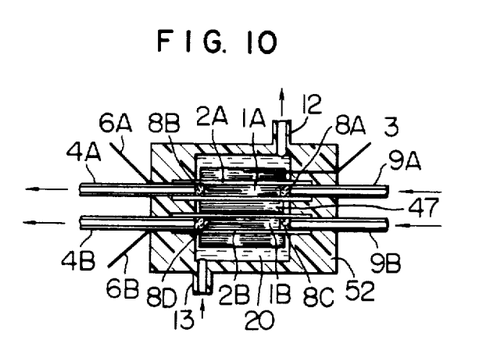
FIG. 10 is a cross-sectional view according to a fourth embodiment of the present invention.

In FIG. 10, a fourth embodiment of the present invention is shown, where the electrolytic cell has a working electrode for a sample and a working electrode for reference.

Working electrodes 1A and 1B are bundles of almost ten thousand of glassy carbon fibers, each having a diameter of 7 μm, packed in cation exchange pipes 2A and 2B having an inner diameter of 0.8 mm, respectively, and filters 8A–8D of porous fluorine resin are provided at both ends of the pipes, and tubes 4A, 4B, 9A and 9B of fluorine resin are connected to the cation exchange pipes. A counterelectrode 47 common to these two working electrodes 1A and 1B is provided around the cation exchange pipes 2A and 2B and all these electrodes are encased in a case 52. A counterelectrode chamber 20 formed in the case 52 has an inlet 13 and an outlet 12 for an electrolytic solution for the counterelectrode. Lead wires 3, 6A and 6B are provided at the respective electrodes. In this manner, a flowthrough-type electrolytic cell with two parallel passages in one and same cell can be provided. Predetermined potentials are applied to between the lead wires 6A and 6B to the respective working electrodes 1A and 1B, and the lead wire 3 to the counterelectrode 7 to selectively electrolyze a desired component. An eluant solution containing electroactive substances is led through the tube 9A at the side of the working electrode 1A for the sample, then through the filter 8A, the working electrode 1A, the filter 8B and the tube 4A to the outside. On the other hand, only an eluant solution is likewise led through the working electrode 1B for the reference, and an electrolytic solution is led into the electrolytic solution chamber for the counterelectrode through the inlet 13 and discharged through the outlet 12. The counterelectrode 47 is a bundle of carbon fibers around the outer surfaces of the ion exchange pipes 2A and 2B, wound by a platinum wire, and the electrolytic solution is an alkaline solution of 0.1 MK$_3$[Fe(CN)$_6$]–0.1 MK$_4$[Fe(CN)$_6$]–0.1M KNO$_3$. The lead wires 6A, 6B and 3 to the respective electrodes are platinum wires, and can be also gold wires. The case 52 is made of silicone rubber, and can be also made of any water-resisting, insulating material.

The flowthrough-type electrolytic cell of two parallel passages according to this embodiment has such an effect that the respective working electrodes 1A and 1B can be used for the individual purposes to serve as two detectors.

Figure 11:
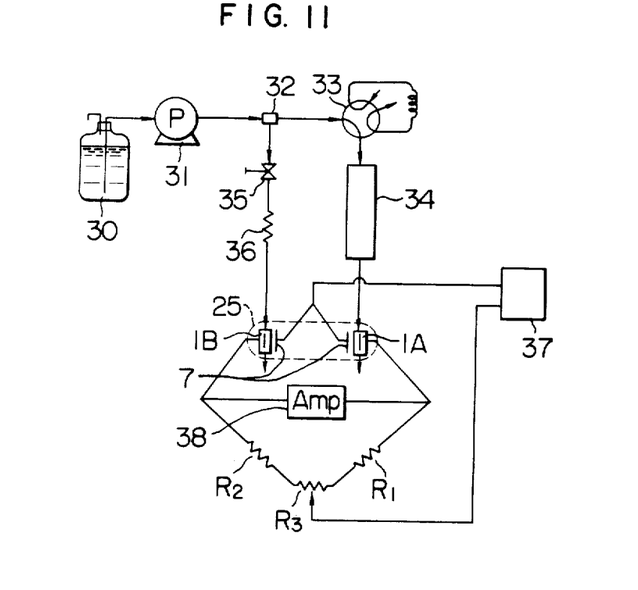
FIG. 11 is an example of conduit and electric circuit diagram of a liquid chromatograph to which the embodiment of FIG. 10 is applied.

In FIG. 11, a flow diagram for effectively utilizing the embodiment of FIG. 10 is shown, where a piping line is so made that an eluant solution 30 is led by a pump 31, on one hand, to the working electrode 1A of the flowthrough-type electrolytic cell of two parallel passages 25 from a branch 32 through a sample feed valve 33 and a separation column 34 and discharged to the outside and, on the other hand to the working electrode 1B of the electrolytic cell 25 from the branch 32 through a flow rate control valve 35 and a resistance tube 36 and discharged to the outside. Electric wiring is so made that the counterelectrode 7 common to both working electrodes 1A and 1B of the electrolytic cell 25 is wired to one terminal of power source 37 on one hand, and the working electrodes 1A and 1B are connected to both ends of a variable resistor R$_3$ for zero adjustment through resistors R$_1$ and R$_2$, respectively, and through an amplifier 38, and the cursor terminal on the variable resistor R$_3$ is wired to the other terminal of the power source 37 on the other hand to form a kind of bridge circuit. The amplifier 38 is connected to a recorder, etc. (not shown on the drawing). In the piping line, the flow rate of an eluant solution to the working electrode 1B is adjusted to a flow rate substantially equal to that of the eluant solution to the separation column 34 by the flow rate control valve 35. On the other hand, in the electric circuit, predetermined potentials are applied to the respective electrodes of the electrolytic cell 25 from the power source 37 to selectively electrolyze a desired component. In the normal state, only the same eluant solution flows through the working electrodes 1A and 1B, and thus the electric currents passing to the working electrodes 1A and 1B are substantially equal to each other. For further equalization, the background current passing through the amplifier 38 in the bridge circuit can be made zero by adjusting the variable resistor R$_3$. This means that, even if an eluant solution is changed by continuous gradient elution or by stepwise gradient elution, the background current passing through the amplifier 38 is zero.

When a sample is introduced into the separation column 34 from the sample feed valve 33, sample components are separated and eluted in the separation column 34 and led to the working electrode 1A of the electrolytic cell 25, where the desired sample components are electrolyzed, and consequently the current at the working electrode 1A is increased. That is, the bridge circuit is brought into imbalance, and only the electrolytic current passes through the amplifier 38.

Figure 12:
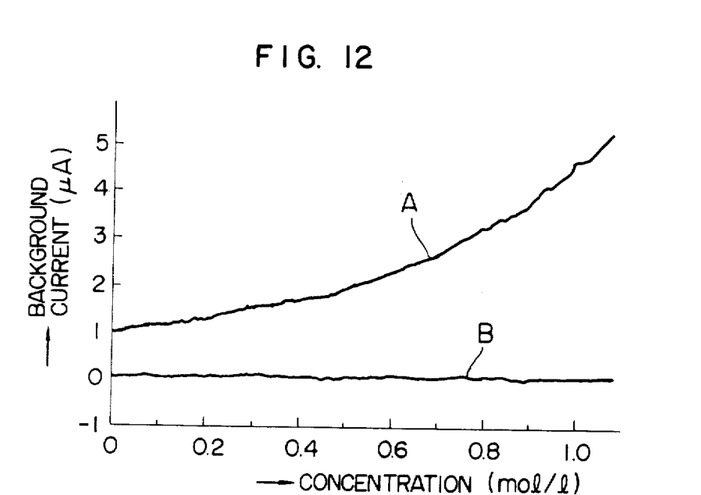
FIG. 12 is a diagram showing test results for confirming base line fluctuations according to the embodiment of FIG. 10.

In FIG. 12, base line of chromatogram according to this embodiment of the present invention is shown, where the axis of abscissa shows a change in concentration of an eluant solution, and the axis of ordinate shows a change in background current. When an ammonium chloride concentration of an eluant solution is changed linearly from zero (water) to 1M, the background current increases in the case of using only one working electrode of the electrolytic cell as in the conventional case, as shown by curve A, and the base line is unstable and a noise increase is observed, whereas in the embodiment of FIG. 10, no change is observed in the background current, as shown by line B in FIG. 12, and no substantial noise increase is observed.

Thus, this embodiment has such an effect that the base line of chromatogram is not changed against a change in the eluant solution composition for the liquid chromatography by outputting only a difference in the electrolytic current passing through both working electrodes of a flowthrough-type electrolytic cell of two parallel passages, as shown in this embodiment. Furthermore, such additional effect that the base line is stable with no noise increase can be obtained.

We claim:

1. A flowthrough-type electrolytic cell, which comprises:

a chamber adapted to contain an electrolyte solution;

pipe means whose one end is communicated with a sample inlet and whose other end is communicated with a sample outlet, said pipe means being made of an ion exchange material, said pipe means being located in said chamber;

a working electrode provided in the pipe means, said working electrode comprising electroconductive material in the form of a bundle of fibers, or particulate matter, packed in the pipe means; and a counterelectrode provided outside the pipe means and within said chamber.

2. A flowthrough-type electrolytic cell according to claim 1, wherein the working electrode comprises a bundle of fibers.

3. A flowthrough-type electrolytic cell according to claim 2, wherein the fibers are fibers and each have a diameter of not more than 100 μm.

4. A flowthrough-type electrolytic cell according to claim 2, wherein the cross-sectional area of the ion exchange pipe means is substantially equal to the cross-sectional area of a conduit for leading a sample to the electrolytic cell.

5. A flowthrough-type electrolytic cell according to claim 2, wherein said bundle of fibers comprises a bundle of glassy carbon fibers.

6. A flowthrough-type electrolytic cell according to claim 5, wherein the bundle of glassy carbon fibers is positioned such that the length of the fibers extends in the longitudinal direction of the pipe means.

7. A flowthrough-type electrolytic cell according to claim 6, wherein the bundle of fibers fills the pipe means.

8. A flowthrough-type electrolytic cell according to claim 2, wherein the bundle of fibers fills the pipe means.

9. A flowthrough-type electrolytic cell according to claim 2, wherein said bundle of fibers is positioned such that the length of the fibers extends in the longitudinal direction of the pipe means.

10. A flowthrough-type electrolytic cell according to claim 1, wherein the pipe means is circular in cross-section and has an inner diameter of not more than 1 mm.

11. A flowthrough-type electrolytic cell according to claim 1, wherein the counterelectrode is in a cylindrical form and surrounds the pipe means.

12. A flowthrough-type electrolytic cell according to claim 11, wherein the counterelectrode comprises a bundle of electroconductive glassy carbon fibers in said cylindrical form.

13. A flowthrough-type electrolytic cell according to claim 1, wherein said chamber includes inlet means and outlet means for flow of electrolyte through said chamber.

14. A flowthrough-type electrolytic cell, which comprises:

a chamber adapted to contain an electrolyte solution;

pipe means whose one end is communicated with a sample inlet and whose other end is communicated with a sample outlet, said pipe means being made of an ion exchange material, said pipe means being located in said chamber;

a working electrode provided in the pipe means, said working electrode comprising an electroconductive material in the form of a bundle of fibers, or particulate matter, packed in the pipe means;

a rod-like material provided in the working electrode; and a counterelectrode provided outside the pipe means and within said chamber.

15. A flowthrough-type electrolytic cell according to claim 14, wherein the rod-like material comprises an electroconductive material and is electrically connected to a working electrode lead wire.

16. A flowthrough-type electrolytic cell according to claim 14, wherein the rod-like material is a material swellable as equally as said ion exchange material through contact with a solution.

17. A flowthrough-type electrolytic cell according to claim 16, wherein the swellable material is a rod of the same material as that of the ion exchange material of the pipe means.

18. A flowthrough-type electrolytic cell according to claim 14, wherein the size of the rod-like material is not more than one-third of the inner diameter of the pipe means.

19. A flowthrough-type electrolytic cell according to claim 14, wherein the shape of the working electrode is cylindrical.

20. A flowthrough-type electrolytic cell according to claim 14, wherein said working electrode comprises a bundle of glassy carbon fibers filled in the pipe means, the length of the bundle of glassy carbon fibers extending in the longitudinal direction of the pipe means.

21. A flowthrough-type electrolytic cell, which comprises:

a chamber adapted to contain an electrolytic solution, at least one part of a wall of said chamber being made of an oxygen-permeable membrane, said at least one part being adapted to be exposed to a source of oxygen;

pipe means whose one end is communicated with a sample inlet and whose other end is communicated with a sample outlet, said pipe means being made of an ion exchange material, said pipe means being located in said chamber;

a working electrode provided in the pipe means; and a counterelectrode provided outside the pipe means and within said chamber.

22. A flowthrough-type electrolytic cell according to claim 21, wherein the electrolytic solution is an aqueous potassium iodide solution.

23. A flowthrough-type electrolytic cell according to claim 21, wherein said working electrode comprises a bundle of glassy carbon fibers filled in the pipe means, the length of the bundle of glassy carbon fibers extending in the longitudinal direction of the pipe means.

24. A flowthrough-type electrolytic cell according to claim 23, wherein said at least one part is adapted to be exposed to the atmosphere.

25. A flowthrough-type electrolytic cell according to claim 21, wherein said at least one part is adapted to be exposed to the atmosphere.

26. A flowthrough-type electrolytic cell according to claim 21, wherein the oxygen-permeable membrane is made of a material selected fromd the group consisting of silicone rubber and polytetrafluoroethylene.

27. A flowthrough-type electrolytic cell, which comprises:

a first pipe means whose one end is communicated with a sample inlet and whose other end is communicated with a sample outlet, said first pipe means being made of an ion exchange material;

a second pipe means for reference, made of the same material as that of the first pipe means;

a chamber containing the first and second pipe means and an electrolytic solution;

a first working electrode provided in the first pipe means;

a second working electrode provided in the second pipe means; and a counterelectrode provided outside the first and second pipe means and in the chamber.

* * * * *